United States Patent [19]

Dietrich

[11] Patent Number: 5,792,207
[45] Date of Patent: Aug. 11, 1998

[54] EXTRACORPOREAL TEST DEVICE FOR AN IMPLANTABLE MEDICAL DEVICE

[75] Inventor: Michael Dietrich, Berlin, Germany

[73] Assignee: Biotronix Mess-und Therapiegeraete GmbH & Co., Berlin, Germany

[21] Appl. No.: 774,856

[22] Filed: Dec. 18, 1996

[30] Foreign Application Priority Data

Dec. 18, 1995 [DE] Germany .................. 195 48 658.7

[51] Int. Cl.$^6$ ............................................. A61N 1/362
[52] U.S. Cl. ............................. 607/32; 607/30; 607/60
[58] Field of Search ............................. 128/697, 899; 607/27, 32, 59, 60, 30; 600/510

[56] References Cited

U.S. PATENT DOCUMENTS

| | | | |
|---|---|---|---|
| 4,757,816 | 7/1988 | Ryan et al. | 128/697 |
| 5,168,871 | 12/1992 | Grevious . | |
| 5,186,169 | 2/1993 | Schaldach | 607/32 |
| 5,411,536 | 5/1995 | Armstrong . | |
| 5,421,830 | 6/1995 | Epstein et al. . | |
| 5,466,246 | 11/1995 | Silvian . | |

FOREIGN PATENT DOCUMENTS

| | | |
|---|---|---|
| 0012709 | 6/1980 | European Pat. Off. . |
| 2545802C2 | 10/1983 | Germany . |
| 3701947A1 | 6/1987 | Germany . |
| 295995A5 | 11/1991 | Germany . |
| 4417927A1 | 11/1995 | Germany . |

Primary Examiner—William E. Kamm
Assistant Examiner—George R. Evanisku
Attorney, Agent, or Firm—Spencer & Frank

[57] ABSTRACT

An extracorporeal apparatus is provided for use with an implantable medical device and has a telemetry unit for receiving a telemetry signal transmitted from the implantable device. The extracorporeal apparatus further includes a transmission member disposed downstream of the telemetry receiver for compensating for the signal influence contained in the telemetry signal and effected by a first transmission member in the implantable device for the purpose of interference-free reproduction of a measuring signal received by way of the implantable device in the body, and/or for simulating the signal influence effected by a second transmission member in the implantable device for the purpose of external modelling of the dependency of the device behavior on the measuring signal.

14 Claims, 2 Drawing Sheets

EXTRACORPOREAL TEST DEVICE FOR AN IMPLANTABLE MEDICAL DEVICE

CROSS-REFERENCE TO RELATED APPLICATIONS

The right of priority is claimed with respect to German application No. 195 48 658.7 filed in Germany on Dec. 18, 1995, the disclosure of which is incorporated herein by reference.

BACKGROUND OF THE INVENTION

The invention relates to an extracorporeal apparatus for use with an implantable medical device, particularly a pacemaker, defibrillator or cardioverter.

The design of a modern medical device that can be adapted to an individual patient's conditions with the use of a programming device typically allows the device to receive signals from inside the body. These may be signals that must be transmitted from the measuring site with the least possible amount of interference, or signals that influence the operating behavior of the implantable device. These signals are influenced by signal-transmission members provided inside the processing part of the implantable device and disposed upstream or downstream of the telemetry stage.

In a modern pacemaker, it is typically the case that the electrical potentials representing the heart action are transmitted in the form of an intracardial electrocardiogram to an extracorporeal device for evaluation and/or recording purposes.

The cardiac action signals that are represented in the intracardial EKG are received by an input filter provided for normal pacemaker operation, and are subsequently further processed. Based on the transmission properties of the pacemaker input filter, particularly the filter's frequency response, the cardiac action signals are altered to a considerable degree, which precludes a reliable diagnosis when evaluated in an EKG device.

German Patent document DE-A-2 545 802 discloses a cardiac signal discriminator that serves to suppress interfering signals that are simultaneously detected with the cardiac action signal. The heart signal discriminator has means for rectifying and simultaneously damping the detected signals.

A digitally-controlled amplitude-control device for electrocardiographic signals is disclosed in European Patent Application No. EP-A-0 012 709, wherein the control device has means for increasing or reducing the transmission factor by one stage following occurrence of a pulse signal (QRS complex) after a comparison of the signal amplitude with a threshold value.

The switching arrangements known from the above-cited documents essentially relate to adapting the amplitude of the intracardial signals in order to at least limit the effect of disturbing or interfering signals. This is necessary, because the amplitude of so-called artifacts is frequently higher by one hundred times than the desired cardiac signal.

A switching arrangement for eliminating pacemaker pulse components from EKG leads is described in DD-A-295 995. With this arrangement, surface EKG signals can be freed from pacemaker pulse components with the use of suitable filtering at the output of the EKG amplifier.

German Patent document DE-A-3 701 947 describes a method of detecting a surface EKG, which is intended to assure reliable processing of the cardiac action signals, even in pacemaker patients, in that the operating parameters of the pacemaker are read out using a wireless signal-transmission device, and then taken into consideration during processing of the surface EKG.

A programming system for a pacemaker or cardioverter/defibrillator having means for recording and analyzing an intracardially-recorded cardiac signal is described in U.S. patent application Ser. No. 5,421,830. In addition to means for storing and reproducing the cardiac signals, this system also includes a simulation of the response of the implanted device to these signals.

The known switching arrangements, however, do not solve the problem of interference in the intracardial EKG by the input filter of the pacemaker. It is possible to transmit the intracardial EKG to an extracorporeal test device, by way of a telemetry transmitter, for differentiated evaluation or storage. The diagnostic value of this intracardial EKG, however, like its usefulness in any simulation of the pacemaker's response, is greatly reduced by the signal-influencing effect of the input filter disposed in the pacemaker, or by that of other transmission members.

Moreover, a problem that exists in the known switching arrangements is that the intracardial EKG is additionally influenced by amplifiers and filters upstream of the point at which it was tapped to be supplied to the telemetry device before the signal prepared in this manner is supplied to a detector device, for example a threshold value detector or processing unit. The signal available at the extracorporeal device is therefore different from the signal present at the input of the detector or processing device inside the pacemaker, so the evaluation of the signal transmitted via the telemetry device does not permit a reliable statement about the detection or processing behavior of the pacemaker.

The above-described problems also exist with respect to external analysis of other body signals that are transmitted outwardly from a tap point in the processing channel in an implanted medical device, as well as signals that are characteristic of a patient's bodily activity.

SUMMARY OF THE INVENTION

It is therefore an object of the invention to provide an extracorporeal apparatus for use with an implantable electromedical device which permits the availability of the truest possible signals and, additionally, with respect to the function of the implanted device, significant further processing of intracorporeally detected signals outside of the body.

The above and other objects are accomplished according to the invention by the provision of a combination of an extra-corporeal apparatus and an implantable electromedical device, wherein the implantable electromedical device includes a processing channel for receiving and processing a measuring signal received by an intracorporeal signal receiver and for influencing the function of the implantable electromedical device, the processing channel including at least one of first and second signal-influencing transmission members, the implantable electromedical device further including a first telemetry unit for transmitting a telemetry signal derived from the measuring signal to the extracorporeal apparatus, the input of the first telemetry unit being connected to at least one of an output of the first transmission member and an input of the second transmission member; and the extracorporeal apparatus includes: a second telemetry unit for receiving the telemetry signal emitted by the implantable electromedical device, a third transmission member disposed downstream of the second telemetry unit for at least one of: (a) compensating for signal influences contained in the telemetry signal effected by the first transmission member for making available a measuring signal outside of the body that is essentially uninfluenced by the first transmission member and (b) simulating a signal influence of the measuring signal caused by the second transmission member for extracorporeal simulating the output signal of the second transmission member for external modelling of the behavior of the implantable device as a function of the measuring signal.

The invention is based upon the principle of using the extracorporeal apparatus to compensate for influences on the signal caused by a transmission member, for example the input filter of a pacemaker, upstream the signal tap point, in order to obtain an interference-free signal, on the one hand and, on the other hand, if necessary, to simulate the signal influence due to amplifiers and filters in the implanted device, between the signal tap point and the actual detector or processing unit, to model the overall detection behavior of the implanted device externally.

The term "input signal" is to be understood hereinafter in a general sense. A particular advantage is that the method of the invention can be applied to natural, that is spontaneous, cardiac action signals, in external processing of intracardial EKGs. The invention can, however, also be used advantageously with body signals that indicate pacemaker activity, for example intrathoracically detected or intracardially detected impedance signals. It is not limited to these applications, however, and can essentially be used for all signals transmitted outwardly from the internal processing channel of an implanted device.

In a pacemaker, the first transmission member disposed in the input channel is usually an input filter configured as, for example, an anti-aliasing filter.

The second transmission member usually comprises an amplifier that has programmable amplification and permits the signal detector to be adapted to the electrical level of the input signal through a setting of the amplification, or a setting of a corresponding programmable amplifier-filter assembly. The transmission members can also respectively comprise a plurality of individual components.

Pacemakers with which embodiments of the device of the invention can advantageously be used have a telemetry transmitter for transmitting the body signal (especially intracardial EKGs) outside of the body. Such a transmitter is connected to a processing channel upstream of the second transmission member and/or downstream of the first transmission member. The telemetry transmitter is typically a component of a telemetry unit of the pacemaker that permits both transmitting and receiving operations. Input signals received by the pacemaker are transmitted in the transmitting operation to the extracorporeal device, while the receiving operation permits programming of the pacemaker using the extracorporeal test device.

If the pacemaker only includes one transmission member, the signal tap for the telemetry transmitter is effected either upstream or downstream of this transmission member.

If, in contrast, the pacemaker includes two or more transmission members (which is typically the case in practice), the signal tap takes place between the transmission members.

In an embodiment oriented to implanted devices, in which the signal tap is effected downstream of a transmission member, the apparatus of the invention has a third transmission member that is disposed downstream of the telemetry receiver in the extracorporeal device which has the task of compensating for the signal influence due to the first transmission member disposed upstream of the telemetry transmitter in the implanted device, usually the input filter, in order to make available the interference-free input signal. This is particularly advantageous in the reception and transmission of an intracardial EKG as an input signal, because an interference-free EKG has much more diagnostic value for the treating physician than the EKG signals detected with the known test devices and distorted by the input filter of the pacemaker. The third transmission member therefore has an exactly inverse transmission function with respect to the first transmission member so that its signal-influencing effect can be compensated to the greatest possible extent.

If the first transmission member in the pacemaker has, for example, the complex transmission function $c_1$ (f), the telemetry signal TS(f) is calculated from the input signal ES(f) according to the formula:

$$TS(f) = c_1(f) \cdot ES(f)$$

The output signal AS(f) of the third transmission member, with the complex transmission function $C_3(f)$, can then be calculated from the telemetry signal TS(f):

$$AS(f) = c_3(f) \cdot TS(f)$$

The transmission function $c_3$ (f) must be selected such that the output signal TS(f) of the third transmission member reproduces the input signal with as little interference as possible. The resulting requirement is:

$$c_3(f) = 1/c_1(f)$$

For an implanted device in which signal tapping takes place upstream of a further transmission member, here the "second transmission member," the signal appearing at the output of the transmission member provided upstream of the tap point is different from the telemetrically-transmitted signal. However, in accordance with an aspect of the invention, a modelling of the pacemaker behavior is possible by also applying the transmission function of the second transmission member to the signal present in the external device. Therefore, in this variation of the invention, the transmission function of the external, third transmission member (again, this term may encompass a plurality of transmission members provided in the extracorporeal apparatus) is identical to that of the second transmission member disposed behind the telemetry transmitter.

In a refinement of this variation, which is of particular practical significance, the provision of means for setting different transmission functions of the third transmission member permits a modelling of the pacemaker behavior without necessitating reprogramming of the pacemaker.

As explained above, the second transmission member disposed in the pacemaker usually includes a programmable amplifier that permits the downstream detector or processing device to be adapted to the level of detected cardiac signals. This is important, because the level of cardiac signals detected by the pacemaker is a function of the position of the electrodes, the resistance of the body tissue and other factors, and is therefore subject to fluctuations that must be taken into account by a setting of the initial amplification.

In known pacemaker systems, this setting is typically effected as follows: the treating physician consecutively programs different initial amplifications and, based on sense markers or the pacemaker behavior, determines whether or not the pacemaker recognizes a signal supplied by the heart ("sensing test"). The problem in this case is that the settings of the initial amplification undertaken during the test already have an effect on the pacemaker behavior, which is often undesirable during the test. Thus, if the initial sensitivity is too high, disturbing signals are already detected erroneously as cardiac actions, so a stimulation that may be necessary per se during the test does not take place. If, in contrast, the initial sensitivity is too low, the spontaneous cardiac actions are not detected, and the pacemaker provides constant stimulation during the test, even though the heart is actually beating sufficiently quickly.

A further drawback of known pacemaker systems is that, while programming the pacemaker, the physician typically sets the initial sensitivity higher than is actually necessary in order to be able to reliably identify a cardiac event, even during fluctuations in intensity. The consequence of this, however, is that the input amplifier of the pacemaker becomes saturated during a cardiac event of normal intensity, so that the amplitude of this cardiac event can no longer be determined.

In an advantageous variation of the invention, a detector device having essentially the same detection behavior as the pacemaker is therefore disposed downstream of the third transmission member. The transmission behavior of the third transmission member can be set to determine the transmission function that permits optimum detection behavior. Since the setting takes place in the extracorporeal apparatus, and not in the pacemaker itself, as in known pacemaker systems, the pacemaker behavior is not influenced during the test. Only after the optimum setting has been determined is it transmitted telemetrically from the external device to the programmable pacemaker and set. The third transmission member preferably comprises a digital filter whose filtering characteristic can be set by predefining a plurality of filter coefficients.

In a useful embodiment as a special test device for an implanted device (particularly a pacemaker, defibrillator and/or cardioverter), the extracorporeal apparatus can be configured as an assembly of a programming device for this type of implanted device or a body-signal-analysis device (such as an EKG or EEG device), or an interface, preferably programmable, by way of which a conventional programming or analysis device can be connected in an essentially function-expanding manner to an implanted device.

Other advantageous refinements of the invention are described in detail below in the description of the preferred embodiment of the invention, with reference to the drawing figures.

DETAILED DESCRIPTION OF THE INVENTION

Figure 1:
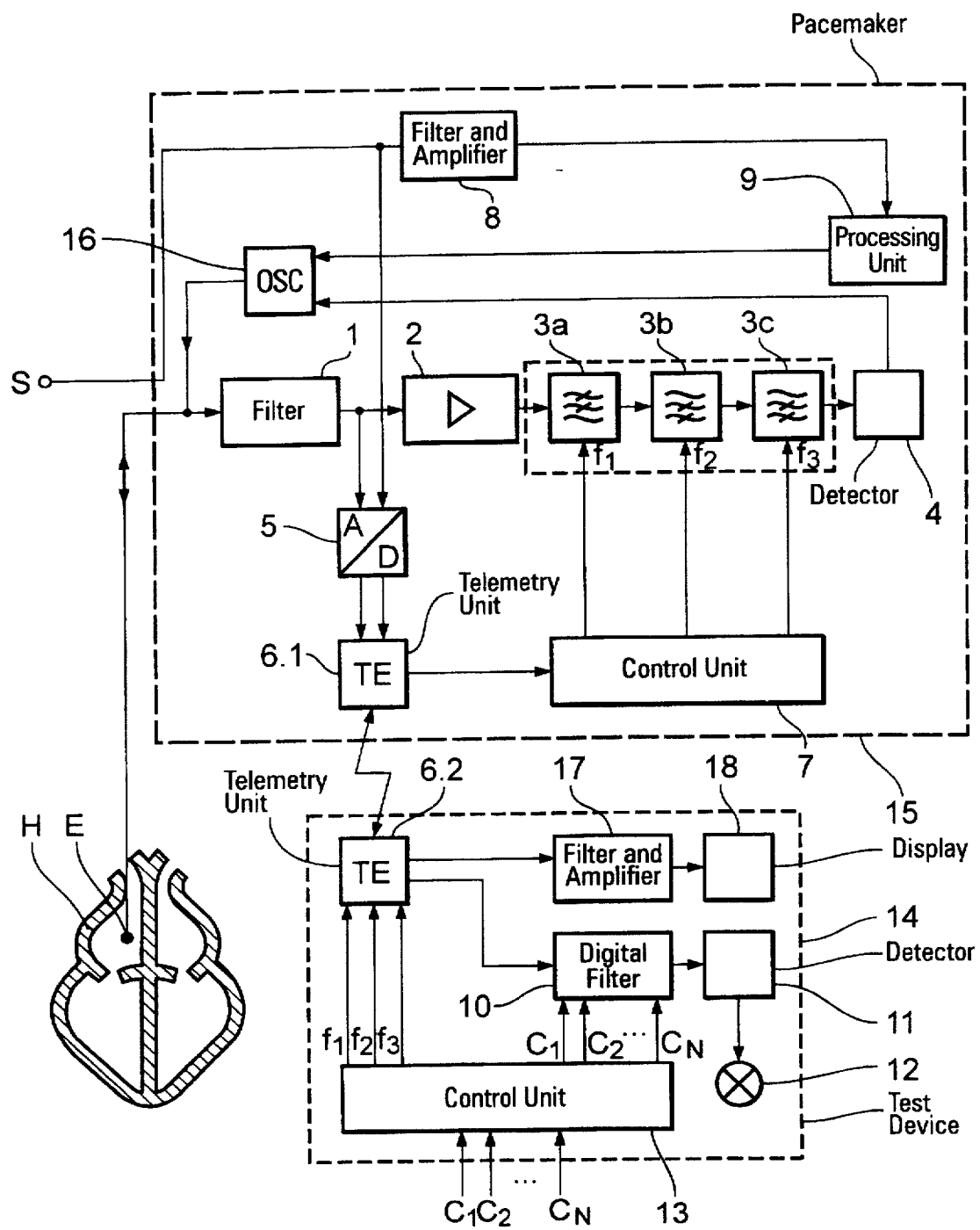
FIG. 1 is a block circuit diagram which shows an extracorporeal test device for use with an implantable pacemaker according to a preferred embodiment of the invention.

Referring to FIG. 1, there is shown a circuit diagram for explaining the design of an extracorporeal test device 14 in connection with a programmable pacemaker 15 in accordance with the principles of the invention. Only the assemblies of the two devices related to the invention are illustrated. Other, conventional components of a pacemaker are presumed to be known and are therefore not shown.

The illustrated pacemaker 15 operates according to the demand principle, i.e., it only transmits stimulation pulses to the heart if the heart does not beat quickly enough or at all. Pacemaker 15 has an electrode E connected to the heart tissue H to detect cardiac signals which are input to an anti-aliasing filter 1 for processing by the pacemaker. In addition to serving as an intracorporeal signal receiver to detect spontaneous cardiac activity, electrode E serves to emit stimulation pulses and is therefore also connected to the output of a pulse generator 16. The output signal of anti-aliasing filter 1 is supplied to an amplifier 2 which amplifies its input signal by a factor of 32.

A transmission member 3 having a plurality of filter elements 3a, 3b, 3c, which have settable cutoff frequencies $f_1$, $f_2$, $f_3$, respectively, is disposed downstream of amplifier 2. Transmission member 3 permits the intracardially-tapped input signal to be adapted to a downstream detector device 4 through the setting of cutoff frequencies $f_1$, $f_2$, $f_3$. Consequently, interfering signals that are received along with the cardiac signals by way of electrode E can be filtered out. Transmission member 3 includes a plurality of control inputs for setting the cutoff frequencies of the individual filter elements 3a, 3b and 3c to set an overall filtering characteristic.

Detector device 4, disposed downstream of transmission member 3, includes as its primary component a bipolar threshold value member which compares the amplified and filtered input signal to positive and negative threshold values, respectively. Detector device 4 detects a natural heartbeat if the input signal exceeds the positive threshold or falls below the negative threshold. Detector device 4 additionally evaluates the temporal sequence and length by which the filtered and amplified input signal exceeds the threshold value in order to prevent an erroneous detection when the signal level is delayed, for example because of the displacement of an electrode in the body of the pacemaker patient, the consequence being a permanent state of exceeding or falling below the threshold value.

Pulse generator 16 is inhibited if detector device 4 detects a natural heartbeat in the above-described manner, and otherwise provides stimulation at a predetermined stimulation frequency (see below). This means that pulse generator 16 restores its internal clock generator and thus only emits a stimulation pulse if no further natural heartbeat is detected within a predetermined time span following detection.

A body detector (another intracorporeal signal receiver), shown outside of the heart, serves to determine a stimulation frequency corresponding to a current hemodynamic need of the patient. Body detector S is configured, in a manner known per se, for example, as an intrathoracic impedance-measuring sensor. Its measuring signal is supplied to an integrated filter and amplifier assembly 8, where signal processing takes place, and travels from there to a processing unit 9, which calculates the stimulation rate from the processed body signal, also in a known way, and controls pulse generator 16 correspondingly.

In addition to the above-described, conventional function as a rate-adaptive demand pacemaker, pacemaker 15 also permits the transmission of an intracardial electrocardiogram (also called "IECG"), as well as the transmission of the signals of body detector S, to extracorporeal test device 14.

To accomplish this, a dual-channel analog/digital converter is connected to an input channel downstream of antialiasing filter 1. This channel intially converts the filtered pacemaker input signal and the measuring signal of body detector S into a digital data word, which permits a subsequent digital data transmission to extracorporeal test device 14.

To this end, pacemaker 15 has a telemetry unit 6.1 which permits both transmitting and receiving operations. In the transmitting operation, the IECG received by way of electrode E, and/or the body sensor signal is transmitted to extracorporeal test device 14, whereas programming signals for setting the operating parameters of pacemaker 15 are received in the receiving operation.

One programming option concerns the programming of the transmission function of transmission member 3, which permits an external adaptation of detector device 4 to the input signal received by electrode E.

Correspondingly, the extracorporeal test device 14 also has a telemetry unit 6.2 which has a receiving operation that permits the reception of the IECG and a transmitting operation that permits the programming of pacemaker 15.

The extracorporeal test device 14 includes, a recursive second order digital filter system 10, which permits filtering of the intracardial EKG signal with a variable filtering characteristic. From the intracardial EKG signal present as a sequence $x_1, x_2 \ldots x_i, \ldots$ of digital sampling values, digital filter 10 calculates a sequence $Y_i, Y_2, \ldots Y_i$ as the output signal according to the formula $$y(n) = \sum_{k=1}^{N} c_k \cdot y(n-k) + \sum_{k=0}^{M} c_{N+1+k} \cdot x(n-k); M \leq N$$

The transmission function of filter 10 is calculated as follows:

$$U(f) = \sqrt{\frac{\left(\sum_{i=1}^{N} c_i \cdot \cos(2 \cdot \pi \cdot f \cdot (i-1))\right)^2 + \left(\sum_{i=1}^{N} c_i \cdot \sin(2 \cdot \pi \cdot f \cdot (i-1))\right)^2}{1 - \left(\sum_{i=N+1}^{M} c_i \cdot \cos(2 \cdot \pi \cdot f \cdot i)\right)^2 + \left(\sum_{i=N+1}^{M} c_i \cdot \sin(2 \cdot \pi \cdot f \cdot i)\right)^2}}$$

The filtering characteristic can be changed within broad boundaries by setting the filter coefficients $c_i$.

The output signal of digital filter 10 is supplied to a detector or processing device 11 inside test device 14 and for possessing the same detection behavior as detector device 4 disposed inside pacemaker 15. The detection behavior of pacemaker 15 is therefore modelled for different filtering characteristics without necessitating reprogramming of the pacemaker itself. To this end, test device 14 has a control unit 13 into which the treating physician enters filter coefficients $c_i$, thereby determining the filtering characteristic of digital filter 10. Control unit 13 then programs these filter coefficients $c_i$ into digital filter 10 so that the treating physician can assess the effects of the filter settings on the pacemaker detection behavior. A display lamp 12, which respectively displays the detection of a cardiac action, checks the detection behavior. Of course, improved processing and storage of the respective detection results are effected in practice so that the effect of different filter settings can be compared.

In addition to the settable digital filter 10, a filter and amplifier unit 17 is also connected to the output of second telemetry unit 6.2. The signal of body sensor S (characterized by encoding during transmission) is supplied to filter and amplifier unit 17 from the telemetry unit. The transmission curve of filter and amplifier unit 17 corresponds to that of filter and amplifier assembly 8 in pacemaker 15, so the influence of the body (e.g. impedance) signal can be simulated externally, in its signal processing path. A further display unit 18, on which the signal corresponding to the input signal of processing unit 9 of the pacemaker can be represented externally is connected to the output of filtering and amplifier unit 17. Means for setting the transmission parameters of filter and amplifier assembly 8 are not shown in the figure, but can be provided in a similar manner and used as described in connection with digital filter 10.

Figure 2A:
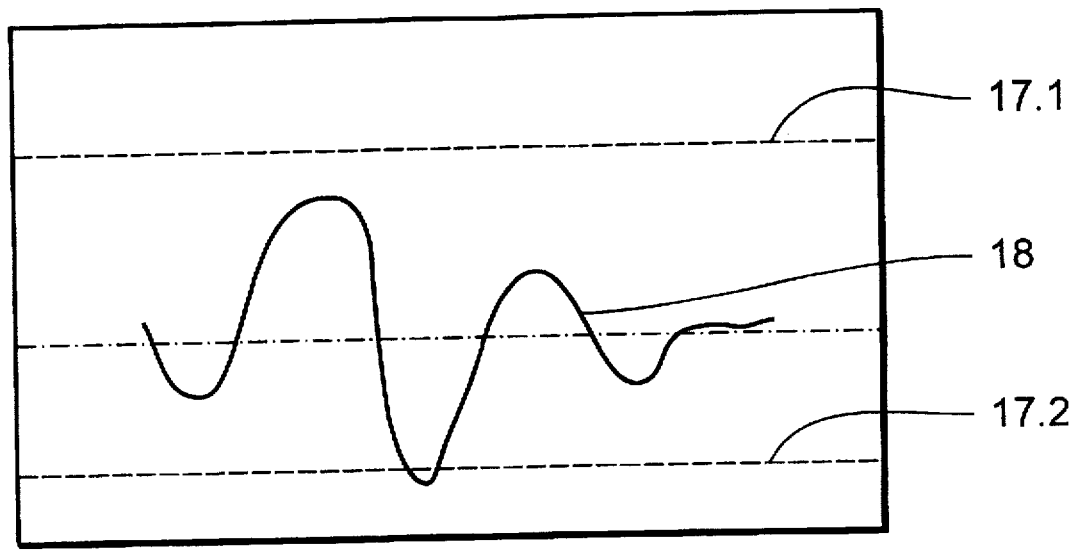
FIG. 2a is a signal diagram which shows an exemplary signal course for the intracardial cardiac signal processed in the pacemaker according to the invention.
Figure 2B:
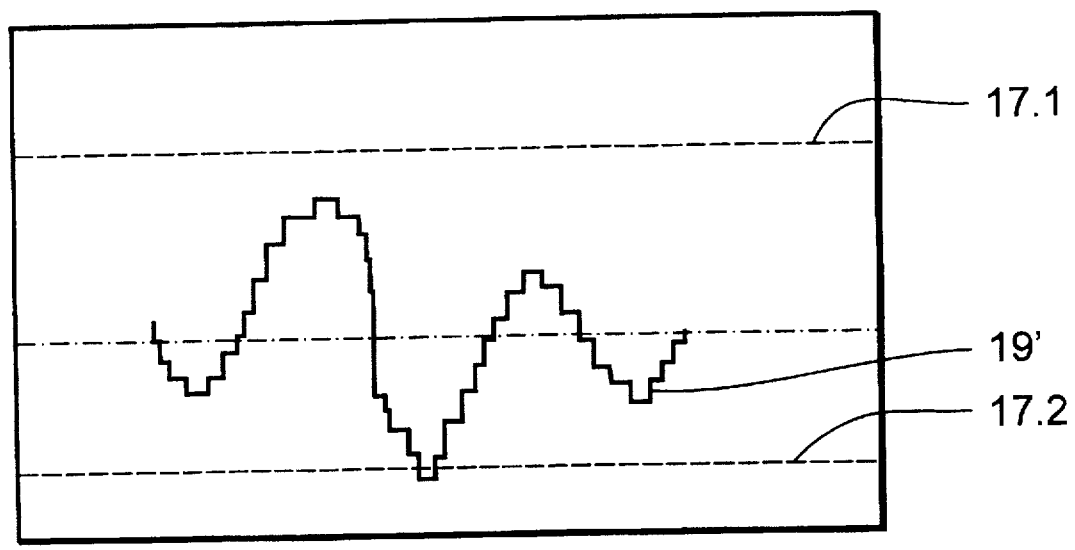
FIG. 2b is a diagram which shows the corresponding signal in the extracorporeal test device according to FIG. 1, in digitized form.

FIG. 2b shows an exemplary signal course for output signal 19' of digital filter 10. The threshold values of the downstream detector device 11 are represented by horizontal, dashed lines 17.1, 17.2. In this signal course, detector device 11 detects a cardiac event, because lower threshold value 17.2 is exceeded.

If the physician has found the optimum filtering characteristic in this way, control unit 13 calculates from this characteristic which values of the cutoff frequencies $f_1, f_2, f_3$ are to be programmed, so that second transmission member 3 disposed in pacemaker 15 optimally simulates the previously determined filtering characteristic.

The values determined in this way are transmitted from telemetry unit 6.2 to a control unit 7 that is disposed in pacemaker 15 and correspondingly sets the three filter elements 3a, 3b, 3c, so that pacemaker 15 exhibits an optimum detection behavior. After cutoff frequencies $f_1, f_2, f_3$ have been programmed, the output signal of second transmission member 3 then exhibits the course 19 shown in FIG. 2a, which coincides with the digitized course 19' simulated by extracorporeal test device 14, as shown in FIG. 2b, with the exception of the discretization.

The invention is not limited in its configuration to the above-described, preferred embodiments. Rather, a number of variations that make use of the illustrated solution, even in fundamentally different embodiments, are conceivable.

The invention has been described in detail with respect to preferred embodiments, and it will now be apparent from the foregoing to those skilled in the art that changes and modifications may be made without departing from the invention in its broader aspects, and the invention, therefore, as defined in the appended claims is intended to cover all such changes and modifications as fall within the true spirit of the invention.

What is claimed is:

1. A combination of an extracorporeal apparatus and an implantable electromedical device, wherein:

the implantable electromedical device includes:

an intracorporeal signal receiver, a processing channel for receiving and processing a measuring signal received by the intracorporeal signal receiver and for influencing the function of the implantable electromedical device, the processing channel including at least one of first and second signal-influencing transmission members, the implantable electromedical device further including a first telemetry unit for transmitting a telemetry signal derived from the measuring signal to the extracorporeal apparatus, the first telemetry unit having an input connected to at least one of an output of the first transmission member and an input of the second transmission member;

the extracorporeal apparatus includes:

a second telemetry unit for receiving the telemetry signal emitted by the implantable electromedical device, a third transmission member disposed downstream of the second telemetry unit for at least one of: (a) compensating for signal influences contained in the telemetry signal effected by the first transmission member for making available a further measuring signal outside of the body that is essentially uninfluenced by the first transmission member and (b) simulating a signal influence of the measuring signal caused by the second transmission member for extracorporeally simulating an output signal of the second transmission member for external modelling of the behavior of the implantable device as a function of the measuring signal; and the third transmission member has a transmission behavior which is inverse with respect to a transmission behavior of the first transmission member to compensate for the signal influence caused by the first transmission member.

2. The combination as defined claim 1, wherein the third transmission member is programmable for setting the transmission behavior of the third transmission member.

3. The combination according to claim 1, wherein the second transmission member includes a plurality of filter elements which have settable cutoff frequencies and the third transmission member comprises a digital filter having a filtering characteristic including filter coefficients that can be set for changing the filter coefficients.

4. The combination as defined in claim 3, wherein the digital filter of the extracorporeal apparatus has a plurality of control inputs and the extracorporeal apparatus further includes a control device having a plurality of outputs connected to the control inputs of the digital filter for setting the filter coefficients of the digital filter.

5. The combination as defined in claim 1, wherein the electromedical device comprises a pacemaker and the second telemetry unit has a transmitting operation for transmitting control commands to the pacemaker to program the pacemaker.

6. The combination as defined in claim 4, wherein the second transmission member is remotely controllable and the implantable electromedical device further includes a first detector device coupled to an output of the second transmission member for detection of the measuring signal; and the extra-corporeal apparatus further includes a second detector device disposed at least indirectly downstream of the third transmission member for extracorporeal detection of the intracorporeally received measuring signal, the second detector device having a detection behavior that is essentially the same as a detection behavior of the first detector device, the transmission behavior of the digital filter being changeable to adapt a detection capability of the second detector device; and the second transmission member in the implantable device is remotely controlled corresponding to the setting of the third transmission member.

7. The combination as defined in claim 1, wherein the intracorporeal signal receiver comprises an intracardial electrode for receiving an intracardial cardiac signal, wherein the measuring signal comprises the intracardial cardiac signal, wherein the implantable electromedical device further comprises a body sensor for receiving a non-cardial body signal, and wherein the non-cardial body signal is coupled by the first telemetry unit to the second telemetry unit.

8. A combination of an extracorporeal apparatus and an implantable electromedical device, wherein:

the implantable electromedical device includes:

an intracorporeal signal receiver, a processing channel for receiving and processing a measuring signal received by the intracorporeal signal receiver and for influencing the function of the implantable electromedical device, the processing channel including at least one of first and second signal-influencing transmission members, the implantable electromedical device further including a first telemetry unit for transmitting a telemetry signal derived from the measuring signal to the extracorporeal apparatus, the first telemetry unit having an input connected to at least one of an output of the first transmission member and an input of the second transmission member;

the extracorporeal apparatus includes:

a second telemetry unit for receiving the telemetry signal emitted by the implantable electromedical device, a third transmission member disposed downstream of the second telemetry unit for at least one of: (a) compensating for signal influences contained in the telemetry signal effected by the first transmission member for making available a further measuring signal outside of the body that is essentially uninfluenced by the first transmission member and (b) simulating a signal influence of the measuring signal caused by the second transmission member for extracorporeally simulating an output signal of the second transmission member for external modelling of the behavior of the implantable device as a function of the measuring signal; and the second transmission member includes a plurality of filter elements which have settable cutoff frequencies and the third transmission member comprises a digital filter having a filtering characteristic including filter coefficients that can be set for changing the filter coefficients.

9. The combination as defined in claim 8, wherein the transmission behavior of the third transmission member essentially corresponds to a transmission behavior of the second transmission member to simulate the signal influence effected by the second transmission member.

10. The combination as defined claim 8, wherein the third transmission member is programmable for setting the transmission behavior of the third transmission member.

11. The combination as defined in claim 8, wherein the digital filter of the extracorporeal apparatus has a plurality of control inputs and the extracorporeal apparatus further includes a control device having a plurality of outputs connected to the control inputs of the digital filter for setting the filter coefficients of the digital filter.

12. The combination as defined in claim 8, wherein the implantable electromedical device comprises a pacemaker and the second telemetry unit has a transmitting operation for transmitting control commands to the pacemaker to program the pacemaker.

13. The combination as defined in claim 11, wherein the second transmission member is remotely controllable and the implantable electromedical device further includes a first detector device coupled to an output of the second transmission member for detection of the measuring signal; and the extracorporeal apparatus further includes a second detector device disposed at least indirectly downstream of the third transmission member for extracorporeal detection of the intracorporeally received measuring signal, the second detector device having a detection behavior that is essentially the same as a detection behavior of the first detector device, the transmission behavior of the third transmission member being changeable to adapt a detection capability of the second detector device; and the second transmission member in the implantable device is remotely controlled corresponding to the setting of the third transmission member.

14. The combination as defined in claim 8, wherein the intracorporeal signal receiver comprises an intracardial electrode for receiving an intracardial cardiac signal, wherein the measuring signal comprises the intracardial cardiac signal, wherein the implantable electromedical device further comprises a body sensor for receiving a non-cardial body signal, and wherein the non-cardial body signal is coupled by the first telemetry unit to the second telemetry unit.

* * * * *

UNITED STATES PATENT AND TRADEMARK OFFICE
CERTIFICATE OF CORRECTION

PATENT NO.     : 5,792,207
DATED          : August 11, 1998
INVENTOR(S)    : Michael Dietrich It is certified that error appears in the above-identified patent and that said Letters Patent is hereby corrected as shown below:

<u>Title page,</u>
Item [73], Assignee: BIOTRONIK Meß– und Therapiegeräte GmbH & Co Ingenieurbüro Berlin, Berlin, Germany Signed and Sealed this Thirtieth Day of July, 2002

Attest:

Attesting Officer

JAMES E. ROGAN
*Director of the United States Patent and Trademark Office*